(12) United States Patent
Barberich

(10) Patent No.: US 7,714,023 B2
(45) Date of Patent: May 11, 2010

(54) TREATMENT OR PROPHYLAXIS OF MIGRAINE OR HEADACHE DISORDERS USING CITALOPRAM, ESCITALOPRAM OR CITALOPRAM METABOLITES

(75) Inventor: Timothy J. Barberich, Concord, MA (US)

(73) Assignee: Sepracor Inc., Marlborough, MA (US)

( * ) Notice: Subject to any disclaimer, the term of this patent is extended or adjusted under 35 U.S.C. 154(b) by 1455 days.

(21) Appl. No.: 11/060,067

(22) Filed: Feb. 17, 2005

(65) Prior Publication Data

US 2005/0192344 A1     Sep. 1, 2005

Related U.S. Application Data

(60) Provisional application No. 60/545,710, filed on Feb. 17, 2004.

(51) Int. Cl.
| | |
|---|---|
| A01N 43/08 | (2006.01) |
| A61K 31/34 | (2006.01) |
| A61K 31/40 | (2006.01) |
| A01N 43/38 | (2006.01) |
| A01N 33/02 | (2006.01) |
| A61K 31/135 | (2006.01) |
| C07D 307/87 | (2006.01) |

(52) U.S. Cl. .................. 514/469; 514/411; 514/649; 514/681; 549/462

(58) Field of Classification Search ............ 514/411, 514/469, 649, 681; 549/462
See application file for complete search history.

(56) References Cited

U.S. PATENT DOCUMENTS

2005/0014848 A1*   1/2005   Marek et al. ............... 514/657

FOREIGN PATENT DOCUMENTS

| GB | 2 392 385 | 3/2004 |
|---|---|---|
| WO | WO 02/076461 A1 | 10/2002 |
| WO | WO 03/072138 A1 | 9/2003 |

OTHER PUBLICATIONS

Vippagunta et al. Advanced Drug Delivery Reviews. 2001. vol. 48, pp. 3-26.*
Baumann et al. European Neuropsychopharmacology, 2002. vol. 12, pp. 433-444.*
Andersen, et al., "Stereospecific determination of citalopram and desmethylcitalopram by capillary electrophoresis and liquid-phase microextraction", J Pharm. Biomed. Anal. 33 pp. 263-273 (2003).
Lampl, et al., "Chronic and episodic tension-type headache: Prophylactic therapy with citalopram", Neuropsychiatrie 1995 Germany, vol. 9, No. 1, pp. 15-19 (1995).
Moretti et al., "Medication-overuse headache: citalopram associated with analgesics withdrawal as possible treatment", J Headache and Pain, vol. 4, No. 3, pp. 152-155 (2003).
Schaer, Juero, "BC-105-a new serotonin antagonist in the treatment of migraine", Study of Headache, vol. 10, No. 2, pp. 67-73 (1970).

* cited by examiner

Primary Examiner—Sreeni Padmanabhan
Assistant Examiner—Samira Jean-Louis
(74) Attorney, Agent, or Firm—Heslin Rothenberg Farley & Mesiti PC

(57) ABSTRACT

Methods for prophylaxis of or treating or preventing migraine or migraine headaches, or other headache disorders include administering to a subject in need of treatment a therapeutically effective amount of citalopram, escitalopram, or a racemic or optically pure citalopram metabolite, or pharmaceutically acceptable salts, solvates, polymorphs, or hydrates thereof.

10 Claims, No Drawings

TREATMENT OR PROPHYLAXIS OF MIGRAINE OR HEADACHE DISORDERS USING CITALOPRAM, ESCITALOPRAM OR CITALOPRAM METABOLITES

CROSS REFERENCE TO RELATED APPLICATION

This application claims priority from U.S. Provisional Application Ser. No. 60/545,710, filed Feb. 17, 2004, the entire contents of which are hereby incorporated by reference.

FIELD OF THE INVENTION

The invention relates to treating or preventing migraine or headache disorders.

BACKGROUND OF THE INVENTION

Migraine is a common, debilitating disorder that affects approximately 15% of the adult population. There are two major types of migraines, migraine without aura, which occurs in 85% of migraineurs, and migraine with aura. Other symptoms associated with migraines include nausea, vomiting, gastrokinetic changes and hypotension.

Current treatments for migraine generally involve two classes of compounds. The first, the ergot alkaloids and related compounds such as ergotamine tartrate, ergonovine maleate, and ergoloid mesylates (e.g., dihydroergocomine, dihydroergocristine, dihydroergocryptine, and dihydroergotamine mesylate (DHE 45)), are thought to act as alpha adrenergic blocking agents with direct stimulating effects on the smooth muscle of peripheral and cranial blood vessels and to produce depression of centralvasomotor centers. The second class of compounds, typified by sumatriptan succinate (distributed under the name IMITREX™ by Glaxo Wellcome, and described in U.S. Pat. No. 4,816,470) are thought to act as serotonin agonists specific for the $5\text{-HT}_1$ receptor subtype. They have some activity as serotonin agonists, though not with the specificity of sumatriptan.

All of these compounds have serious adverse effects and require supervised administration at efficacious doses. All are administered as injections, the ergot alkaloids as an intramuscular injection, and sumatriptan as a subcutaneous injection. Intravenous injection of either may result in coronary vasospasm, and all are contraindicated for patients suffering from uncontrolled hypertension due to these vasoconstrictive properties. Patients taking either type of compound frequently complain of nausea, chest tightness and other adverse effects; unwanted side effects of sumatriptan include coronary vasospasm, hypertension and angina. Recent evidence suggests that the observed sumatriptan-mediated contraction of coronary arteries may be due to the stimulation of the $5\text{-HT}_{1B}$ (formerly $5\text{-HT}_{1Dbeta}$) subtype of the 5-HT receptors (Kaumann, A. J. Circulation, 1994, 90:1141-1153).

Furthermore, it has been reported that of the 50 to 70% of patients who experience migraine symptom relief within two hours after receiving conventional antimigraine agents, 30-50% experience migraine symptoms again within the next 24 hours. These subsequent headaches are typically termed "rebound," "relapse," "recurrent" or "secondary" headaches.

A variety of analgesics have also been administered to migraine patients. For example, K. M. A. Welch (New Eng. J. Med. 329:1476-1483 (1993)) sets forth the following dosages of analgesics as being useful: aspirin, 500-650 mg; acetaminophen, 500 mg; naproxen sodium, 750-825 mg; tolfenamic acid, 200-400 mg; and ibuprofen, 200 mg. However, these agents are rarely effective in providing complete relief of symptoms and, after initial remission, migraine symptoms often return. The problems that occur with migraine headaches may also be present in other types of headache as well. In all cases, an ideal therapy would reduce or eliminate the symptoms associated with the initial attack and minimize the frequency of later recurrences.

Given the incidence of migraine in the population and the potential side effect liability of current methods of treating migraine, there remains a need for other methods and therapeutic agents for treatment of migraine.

Other types of primary headache disorders include tension headache, cluster headache and miscellaneous-type headache (The International Headache Society, Classification and Diagnostic Criteria for Headache Disorders, Cranial Neuralgias and Facial Pain). Existing therapies for headache disorders include, for example, non-steroidal anti-inflammatory drugs, steroids, narcotics, beta-blockers, antidepressants, and anxiolytics. However, existing therapies fare not truly effective, or they are associated with undesirable side effects, thus there continues to be a need for therapeutic agents for treatment of other headache disorders, such as tension headache and cluster headache.

SUMMARY OF THE INVENTION

It has now been unexpectedly found that that citalopram, escitalopram, racemic and optically pure citalopram metabolites are effective for the prophylaxis of or in preventing and/or treating migraine or other headache disorders, without producing the vasoconstricting side effects of conventional treatments. Accordingly, the present invention relates to methods for treating or preventing migraine, or migraine prophylaxis, wherein citalopram, escitalopram, or a racemic or optically pure citalopram metabolite, or a pharmaceutically acceptable salt, solvate, polymorph, or hydrate thereof, is administered to a subject in need of treatment therefor.

Another embodiment of the present invention relates to methods for treating or preventing tension headache, comprising administering to a subject in need of treatment a therapeutically effective amount of citalopram, escitalopram, or a racemic or optically pure citalopram metabolite, or pharmaceutically acceptable salt, solvate, polymorph, or hydrate thereof. A further embodiment of the present invention relates to methods for treating or preventing cluster headache, comprising administering to a subject in need of treatment a therapeutically effective amount of citalopram, escitalopram, or a racemic or optically pure citalopram metabolite, or pharmaceutically acceptable salt, solvate, polymorph, or hydrate thereof.

A further embodiment of the present invention relates to a method for treating or alleviating pain associated with a headache disorder comprising administering to a subject in need thereof a therapeutically effective amount of citalopram, escitalopram, or a racemic or optically pure citalopram metabolite, or pharmaceutically acceptable salt, solvate, polymorph, or hydrate thereof.

DETAILED DESCRIPTION OF THE INVENTION

Migraine or migraine headache is characterized by pain that starts as a dull pain frequently on one side of the head and builds to a throbbing pain, although the pain may be on both sides of the head, in the back of the neck, or in the face, eye area, or sinuses. This pain may disrupt normal activity and/or may be aggravated by routine activity. Other symptoms may include but are not limited to nausea or vomiting; sensitivity to light, sound and/or smells; stuffy or runny nose and watery eyes; dizziness; numbness, such as facial numbness; confusion or inability to think or speak normally; mood changes; seeing spots; aura: blind spots; flashing lights; tunnel vision; and constipation/diarrhea.

Cluster headache (also known as histamine headache, histamine cephalalgia, Raedar's syndrome, or sphenopalatine neuralgia) is vascular headache syndrome that is often characterized by a series short-lived attacks of pain. Cluster headaches are a grouping of headaches, occurring on a regular basis one or more times day usually over a period of several weeks, with each headache typically brief in duration, usually lasting a few moments to 2 hours, then often followed by a pain-free period. Cluster headaches are usually severe and unilateral, and the pain is typically located at the temple, eye, forehead, cheek, and/or periorbital region. Up to half of patients suffering cluster headaches may also experience tenderness at the base of the skull and neck on the same side as the headache pain.

Two forms of cluster headache include (1) acute form, or episodic clusters with attack phases lasting 4-16 weeks followed by a cluster headache or pain-free interval of six (6) months to years, and (2) chronic form, in which the cluster headache or pain-free interval is less than 1 week in a twelve-month period.

Cluster headache is more commonly seen in males than females, usually beginning in middle adult life, with the mean age of onset in men being 30 years old and later in life for women. Cluster headache typically, though not always, occurs in patients who are also migraine sufferers.

Tension-type or tension headache is the most common headache disorder. This type of headache disorder is not well understood, and many other names have been used to refer to this type of headache disorder, including without limitation ordinary headache, muscle contraction headache, depressive headache, psychogenic headache, and essential headache. In general, tension headache involves diffuse, usually mild to moderate pain of the head, and may also cause pain in the back of the neck, at the base of the skull, or both. The pain associated with tension headache is often described as a tight band around the head.

Tension headaches can last from thirty minutes to an entire week or longer, and can be experienced occasionally, or nearly all the time, and are generally classified into episodic and chronic forms. Episodic and chronic tension headaches are distinguished between occasional headaches and frequent headaches that can occur almost daily.

Episodic tension headache are usually brief, lasting a few minutes to a few hours, and occur less than fifteen days a month. Many patients experiencing episodic tension headache have scalp and neck muscle tenderness in addition to head pain, and patients that suffer increasingly frequent attacks of episodic tension headache are at higher risk for developing chronic tension headache. Chronic tension headache occurs on fifteen days a month or more for at least three months, and can sometimes occur almost continuously, and for a number of years. Chronic tension headache occurs is twice as common in women than men, and is less common than the episodic form.

It has now been discovered that citalopram, escitalopram, and racemic or optically pure citalopram metabolites, or a pharmaceutically acceptable salt, solvate, polymorph, or hydrate thereof, are superior agents for the prophylaxis of or preventing and/or treating migraine, while exhibiting fewer or less severe side effects than conventional treatments. Accordingly, the present invention relates to methods for the prophylaxis of or methods for treating or preventing migraine wherein citalopram, escitalopram, or a racemic or optically pure citalopram metabolite, or a pharmaceutically acceptable salt, solvate, polymorph, or hydrate thereof, is administered to a subject in need of treatment therefor.

Citalopram and escitalopram are selective serotonin reuptake inhibitors (SSRI) indicated for treatment of depression. Citalopram 1 is a racemic mixture of an enantiomeric pair of bicyclic phthalanes, designated (±)-1-(3-dimethylaminopropyl)-1-(4-fluorophenyl)-1,3-dihydroisobenzofuran-5-carbonitrile. Escitalopram 2 is the pure S-enantiomer, designated S-(+)-1-(3-dimethylaminopropyl)-1-(4-fluorophenyl)-1,3-dihydroisobenzofuran-5-carbonitrile.

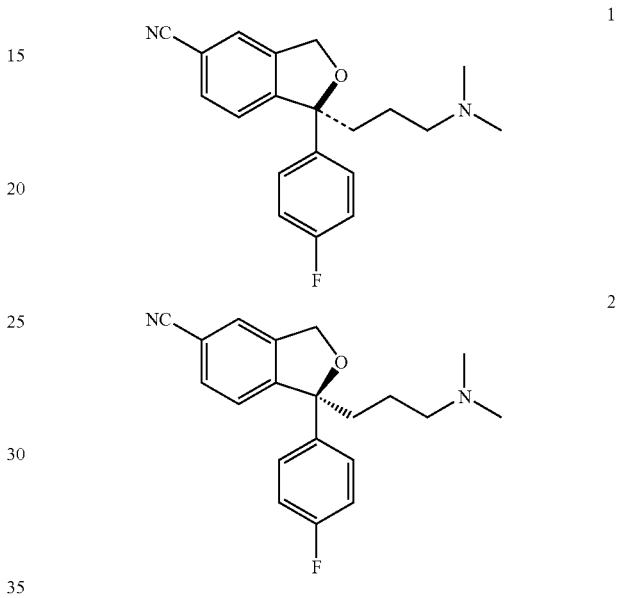

Methods for making citalopram and escitalopram are described in the art, including, e.g., U.S. Pat. Nos. 4,136,193, 4,943,590, and RE 34,712, all of which are incorporated by reference herein in their entirety.

The graphic representations of racemic, ambiscalemic and scalemic or enantiomerically pure compounds used herein are taken from Maehr, *J. Chem. Ed,* 62, 114-120 (1985). Under this scheme, solid and broken wedges denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Racemic desmethylcitalopram can be synthesized by a method which comprises contacting, preferably sequentially, the commercially available phthalide with two Grignard reagents, followed by effecting ring closure, acidic hydrolysis, and a subsequent reductive amination step, as shown in Scheme 1. The preferred Grignard reagents are 4-fluorophenyl magnesium bromide and ethyldioxolane magnesium bromide. In certain embodiments, the reagent used to effect ring closure is mesyl chloride. The preferred reagents for reductive amination are methylamine and sodium borohydride. The resultant amine can be isolated as is or reacted with an acid, such as L-tartaric acid, to form a salt or with a metal to form a metal complex. Synthesis can also be performed such that any or all steps of the synthesis are carried out on a solid support or in a combinatorial fashion.

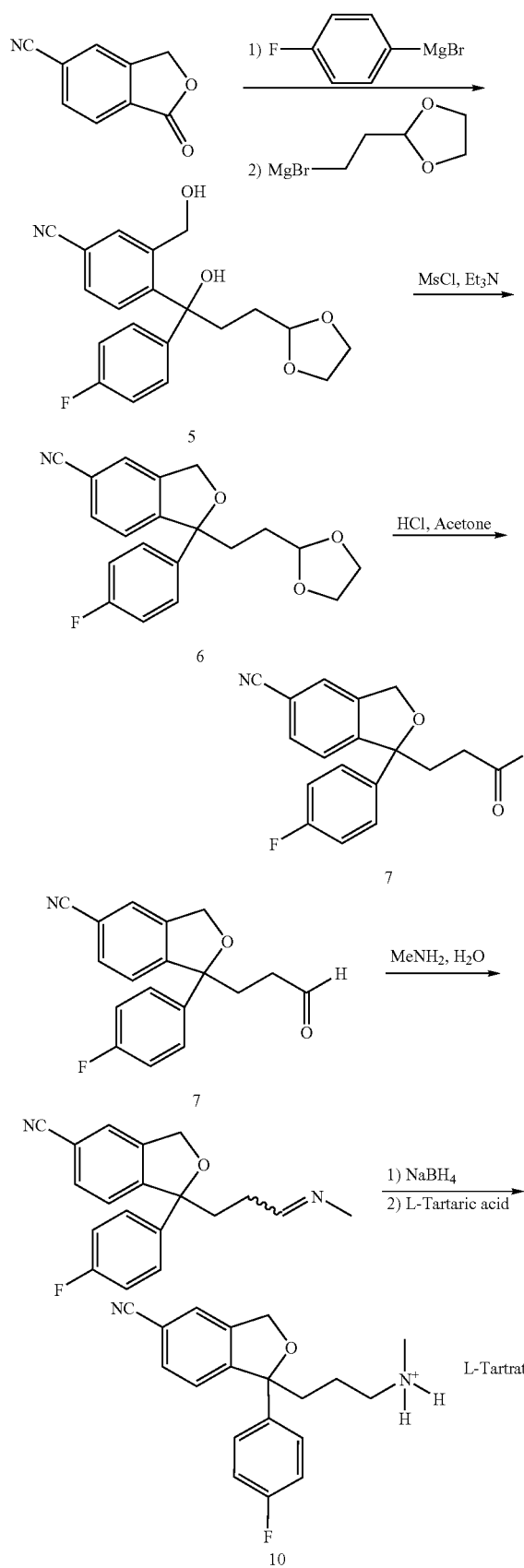

A method for preparing enantiomerically enriched (−)-desmethylcitalopram and (+)-desmethylcitalopram comprises contacting the commercially available phthalide with two Grignard reagents, wherein the second Grignard reagent uses a chiral ligand (by screening many to obtain one with high ee) to give the enantiomerically enriched tertiary alcohol. Ring closure and subsequent reaction are as shown in Scheme 2. The resultant amine is isolated as is or is reacted with an acid to form a salt, such as L-tartaric acid, or with a metal to form a metal complex. Any or all steps of the synthesis can be carried out on a solid support or in a combinatorial fashion.

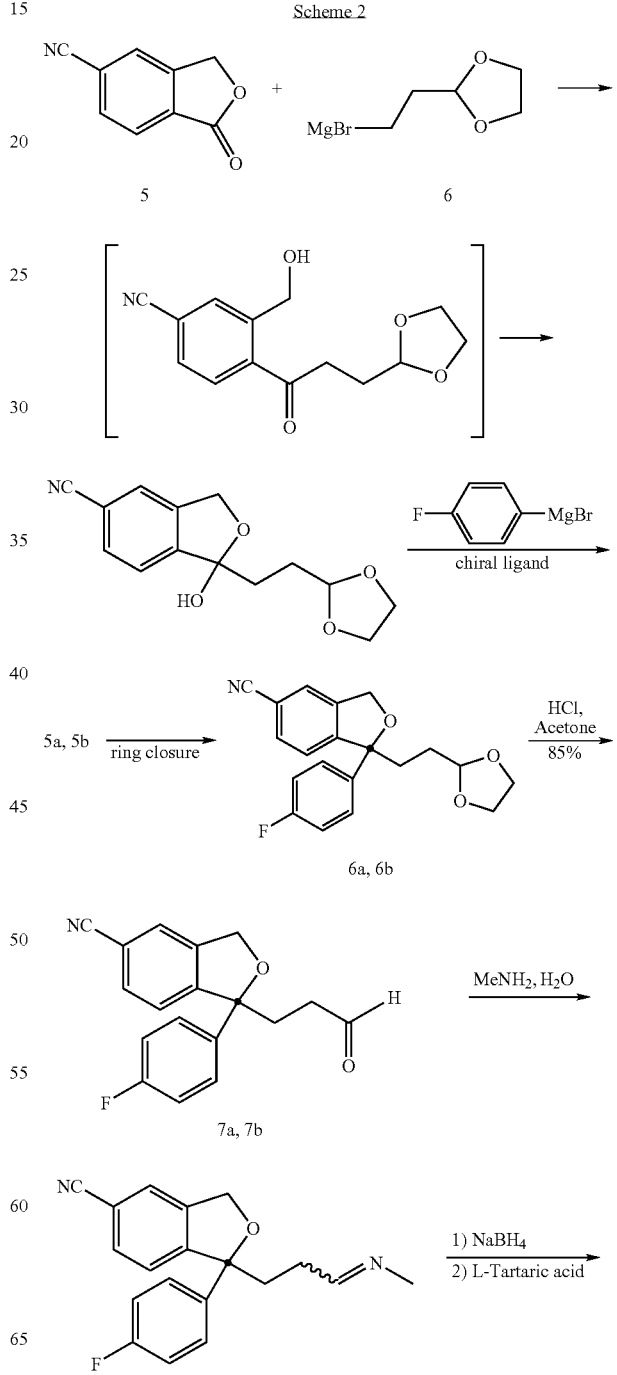

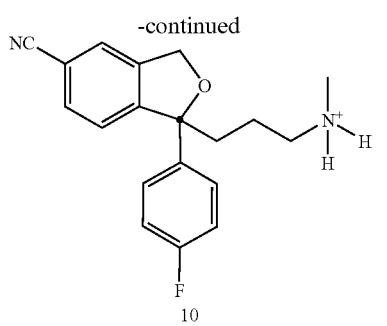

A method for preparing enantiomerically enriched (−)-desmethylcitalopram and (+)-desmethylcitalopram includes chiral column chromatography resolution of the racemic ketal 6. In one embodiment, a CHIRALCEL OD=column with methanol as eluent is used to resolve the corresponding enantiomers (6a and 6b) as shown in Scheme 3. Subsequent reactions of compound 6a and 6b are the same as in Scheme 2 above.

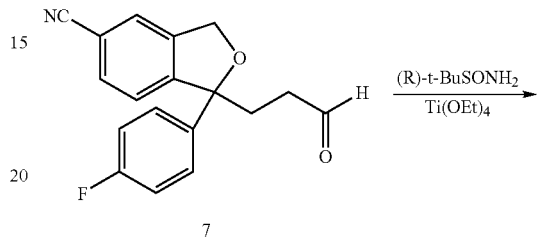

A method for preparing racemic didesmethylcitalopram is reductive amination of aldehyde 7 with an ammonia equivalent followed by hydride reduction as shown in Scheme 4. The resultant product can be isolated as a salt. The preferred ammonia equivalent is (−)-tert-butylsulfinamide, which is contacted with aldehyde 7 in the presence of an alkoxy titanium reagent. The preferred reductant is sodium borohydride. In one embodiment of the invention, the resultant amine is isolated as is or is reacted with an acid to form a salt or with a metal to form a metal complex. In one embodiment, the acid used to prepare a salt is L-tartaric acid. In one embodiment of the invention, any or all steps of the synthesis are carried out on a solid support or in a combinatorial fashion.

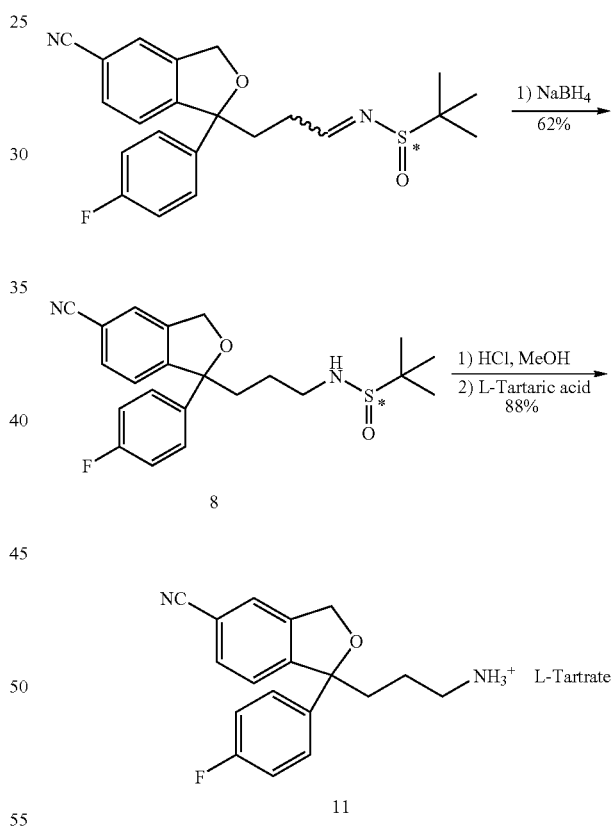

A method for preparing enantiomerically enriched didesmethylcitalopram is by derivatizing racemic didesmethylcitalopram with BOC-anhydride, followed by column chromatography resolution of the racemic BOC-didesmethylcitalopram as shown in Scheme 5. Subsequent acidic hydrolysis of the BOC-derivatized enantiomers yields enantiomerically enriched didesmethylcitalopram. The preferred separation conditions are CHIRALCEL OD column with methanol as eluent.

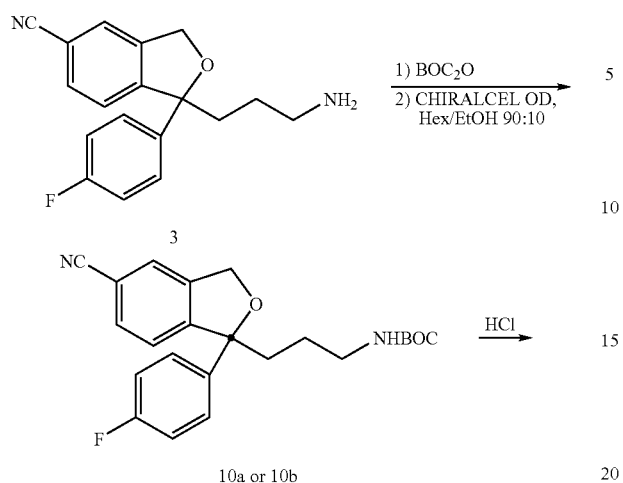
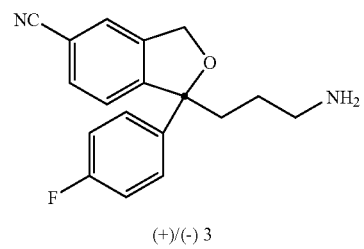
A versatile method for preparing enantiomerically enriched metabolites of citalopram comprises contacting aldehyde 7 with a variety of reagents as shown in Scheme 6.
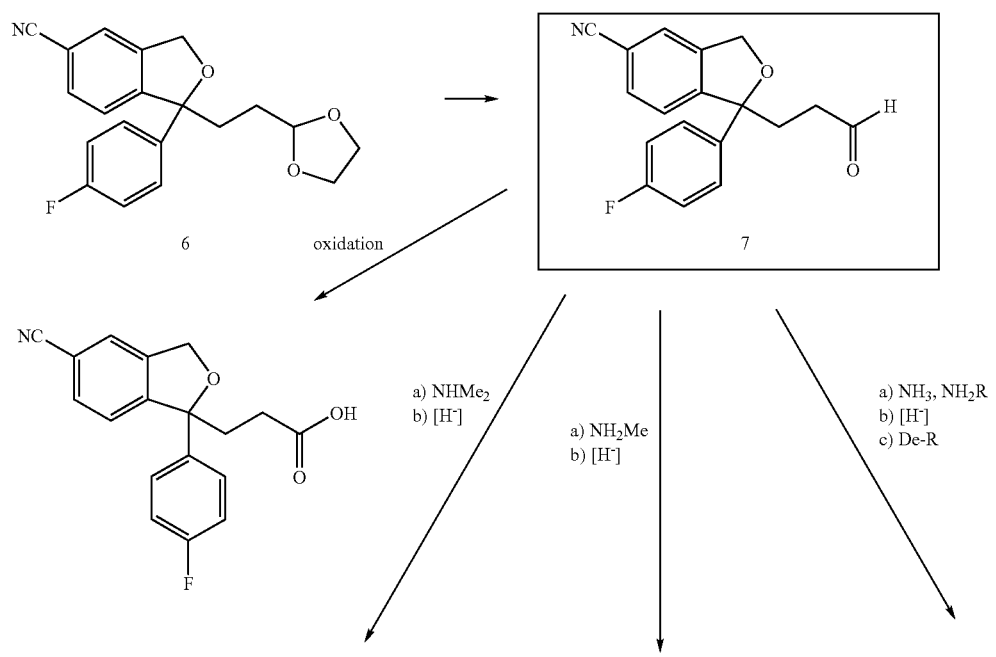
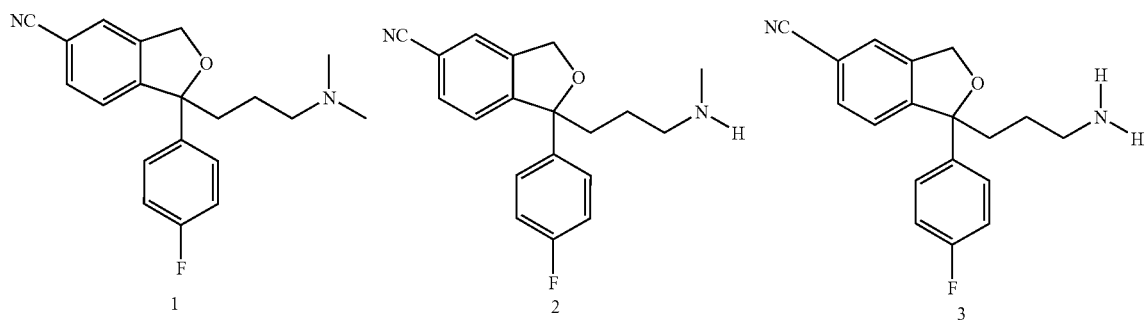

Danish pharmaceutical firm H. Lundbeck A/S developed both citalopram and escitalopram and now markets these in Europe as CIPRAMIL® and CIPRALEX®, respectively. In the United States, Forest Laboratories supplies citalopram as CELEXA® and escitalopram as LEXAPRO® under license from Lundbeck. CELEXA® and LEXAPRO® are available in 10 and 20 mg tablets and as an oral solution; CELEXA® is also available in 40 mg tablets.

In humans, citalopram is stereoselectively metabolized in the liver to the polar metabolites, partially by N-demethylation to desmethylcitalopram (DCIT) and didesmethylcitalopram (DDCIT), as well as by deamination to a propanoic acid metabolite (CIT-PROP) and by N-oxidation to CIT-N-oxide (Baumaim et al, 1995).

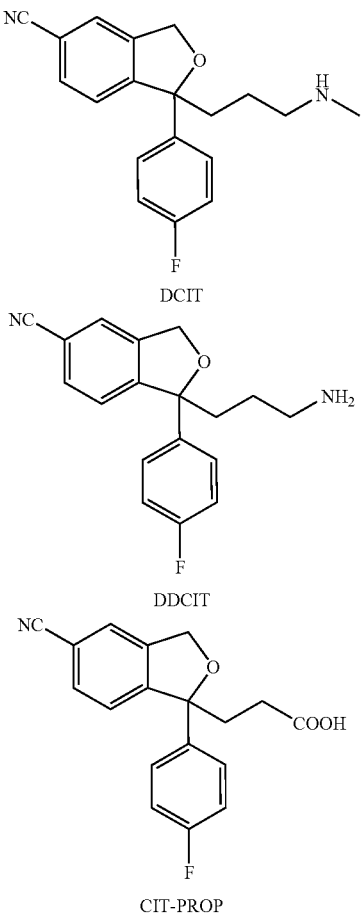

Biotransformation of citalopram has been attributed (in vitro) to the specific human hepatic cytochrome enzymes P450 4A, P4502C19 and, to a minimal extent, P450 2D6 (Willets, 1999). Neither citalopram nor its metabolite desmethylcitalopram inhibit the activity of these or other cytochrome P450 enzymes (P4501A2, P450 2C9, P450 2E1) by more than a mild degree. Citalopram's negligible affinity for receptors for various neurotransmitters (e.g., acetylcholine, histamine, norepinephrine, and dopamine), enzymes (e.g., monoamine oxidase), and other reuptake sites (dopamine and norepinephrine) is thought to account for its relative safety and tolerability, as well as its growing popularity among physicians prescribing antidepressants (Willets, 1999). Furthermore, citalopram's negligible effects on P450 enzymes contribute to the drug's safety in view of drug-drug interactions with other substrates.

Preparation of desmethylcitalopram and didesmethylcitalopram, and isolation of each optically pure enantiomer thereof, is set forth below in the Examples section. Synthesis of all three citalopram metabolites is described in WO 03/040121, which is hereby incorporated by reference in its entirety.

The terms "prophylaxis of", "method of treating or preventing", "method of treating", and method of preventing" when used in connection with migraine mean the amelioration, prevention or relief from the symptoms and/or effects associated with therewith.

The term "migraine" as used herein includes without limitation, migraine, migraine headache, migraine without aura, and migraine with aura.

The term "tension headache" as used herein includes without limitation tension headache, tension-type headache, ordinary headache, muscle contraction headache, depressive headache, psychogenic headache, and essential headache. Tension headaches include headache disorders characterized by diffuse, mild to moderate pain in the head, with or without pain in the back of the neck and/or at the base of the skull.

The term "chronic tension headache" as used herein means a tension headache that lasts or occurs for half of all days or more. Typically, chronic tension headache will occur the majority the days in a month for several consecutive months or longer.

The term "episodic tension headache" as used herein means a tension headache that occurs on fewer than half of all days. Typically, for episodic tension headaches, the pain associated with each episode is relatively brief, lasting a few minutes to a few hours.

As used herein, the term "cluster headache" includes without limitation cluster headache, histamine headache, histamine cephalalgia, Raedar's syndrome, and sphenopalatine neuralgia). Cluster headache is often characterized by a series of short-lived attacks of pain, and a grouping of headaches, occurring on a regular basis one or more times day usually over a period of several weeks or longer.

The term "headache disorder" as used herein includes without limitation, migraine, tension headache, cluster headache, and miscellaneous-type headache.

As used herein, the term "pain" includes without limitation, acute pain, chronic pain, somatogenic pain, and neuropathic pain.

As used herein, the term "citalopram metabolite" includes without limitation, desmethylcitalopram, didesmethylcitalopram, and citalopram propanoic acid, including racemic or optically pure enantiomers thereof, and pharmaceutically acceptable salts, solvates, or hydrates of the same. In one embodiment, the citalopram metabolite is (±)-desmethylcitalopram, optically pure (−)-desmethylcitalopram, or optically pure (+)-desmethylcitalopram, or a pharmaceutically acceptable salt, solvate, polymorph, or hydrate thereof. In another embodiment, the citalopram metabolite is (±)-didesmethylcitalopram, optically pure (−)-didesmethylcitalopram, or optically pure (+)-didesmethylcitalopram, or a pharmaceutically acceptable salt, solvate, polymorph, or hydrate thereof.

As used herein, the term "optically pure" means that the compounds and compositions for use in the methods of the present invention contain a significantly greater proportion of the specified enantiomer in relation to the non-specified enantiomer. For example, optically pure (−)-desmethylcitalopram contains a significantly greater proportion of the (−)-enantiomer in relation to the (+)-enantiomer. In a preferred embodiment, compositions including the optically pure metabolites contain at least 90% by weight of the specified enantiomer and 10% by weight or less of the non-specified enantiomer. More preferably, such compositions contain at least 95% by weight of the specified enantiomer and 5% by weight or less of the non-specified enantiomer. Even more preferably, such compositions contain at least 99% by weight of the specified enantiomer and 1% by weight or less of the non-specified enantiomer. These percentages are based upon the total amount of the citalopram metabolite.

Pharmaceutical compositions for use in the methods of the present invention contain a therapeutically effective amount of citalopram, escitalopram, or a racemic or optically pure citalopram metabolite, or a pharmaceutically acceptable salt, solvate, polymorph, or hydrate thereof. A pharmaceutically acceptable carrier may also be included. Other therapeutic ingredients may also be included. The term pharmaceutically acceptable salts refer to salts prepared from pharmaceutically acceptable non-toxic acids including inorganic acids and organic acids. Examples of acids that form pharmaceutically acceptable salts with citalopram, escitalopram, or a racemic or optically pure citalopram metabolite include acetic acid, benzenesulfonic (besylate) acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, oxalic acid, pamoic acid, pantothenic acid, phosphoric acid, succinic acid, sulfuric acid, tartaric acid and p-toluenesulfonic acid.

Compositions containing citalopram, escitalopram, or a racemic or optically pure citalopram metabolite, or a pharmaceutically acceptable salt, solvate, polymorph, or hydrate thereof, may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt, solvate, polymorph, or hydrate thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 0.5 mg/day to about 500 mg/day, preferably about 1 mg/day to about 250 mg/day, and more preferably, about 5 mg/day to about 100 mg/day, in single or divided doses. It is further recommended that children, patients over 65 years old, and those with impaired renal or hepatic function, initially receive low doses and that the dosage be titrated based on individual responses and blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Any suitable route of administration may be employed for providing the subject with an effective dosage of citalopram, escitalopram, or a racemic or optically pure citalopram metabolite. Actual dosage levels of the active ingredients may be varied so as to obtain an amount of the active ingredient effective to achieve the desired therapeutic response for a particular patient, composition, and mode of administration without being toxic to the patient. The selected dosage level will depend upon a variety of factors including the activity of the compound employed, or the salt, solvate, polymorph, or hydrate thereof, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of citalopram, escitalopram, a racemic or optically pure citalopram metabolite at levels lower than that required in order to achieve the desired therapeutic effect and gradually increase the dosage until the desired effect is achieved.

In general, a suitable daily dose of citalopram, escitalopram, or a racemic or optically pure citalopram metabolite will be that amount of the compound which is the lowest dose effective to produce a therapeutic effect. Such an effective dose will generally depend upon the factors described above. Generally, intravenous, intracerebroventricular and subcutaneous doses of citalopram or escitalopram for a patient will range from about 0.0001 to about 100 mg per kilogram of body weight per day. If desired, the effective daily dose may be administered daily in two, three, four, five, six or more sub-doses administered separately at appropriate intervals, optionally, in unit dosage forms. A physician or veterinarian having ordinary skill in the art can readily determine the total duration of the treatment regime.

The phrases "therapeutically effective amount" or "prophylactically effective amount" as used herein mean that amount of a compound, material, or composition which is effective for producing some desired therapeutic, preventative, or prophylactic effect in at least a sub-population of cells in an animal and thereby blocking the biological consequences of that pathway in the treated cells, at a reasonable benefit/risk ratio applicable to any medical treatment.

As used herein, the terms "subject" or "patient" refers to an animal, preferably a mammal, and most preferably a human.

Suitable routes of administration include orally, nasally, as by, for example, a spray, rectally, intravaginally, parenterally, intracisternally, and topically, as by powders, ointments or drops, including buccally and sublingually. "Parenteral" refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion. Regardless of the route of administration selected, compositions containing citalopram, escitalopram, or a racemic or optically pure citalopram metabolite may be formulated into pharmaceutically acceptable dosage forms such as described below or by other conventional methods known to those of skill in the art, such as those described in *Remington's Pharmaceutical Sciences* (Remington's Pharmaceutical Sciences. Mack Publishing Company, Easton, Pa., USA 1985).

Formulations suitable for oral administration may be in the form of capsules (including hard and soft gelatin capsules), caplets, cachets, pills, tablets, lozenges (using a flavored basis, usually sucrose and acacia ortragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, each containing a predetermined amount of a compound of the present invention as an active ingredient. A compound of the present invention may also be administered as a bolus, electuary or paste.

In solid dosage forms for oral administration (capsules, caplets, tablets, pills, dragees, powders, granules), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Tablets and other solid dosage forms for use in the methods of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient (s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacantli, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredient. Formulations which are suitable for vaginal administration also include pessaries, tampons, creams, gels, pastes; foams or spray formulations containing such carriers as are known in the art to be appropriate.

Dosage forms for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required. The ointments, pastes, creams and gels may contain, in addition to an active compound, excipients, such as animal and vegetable fats, oils, waxes, paraffins, starch, tragacanth, cellulose metabolites, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the composition in the proper medium. Absorption enhancers can also be used to increase the flux of the composition across the skin. The rate of such flux can be controlled by either providing a rate controlling membrane or dispersing the compound in a polymer matrix or gel. Ophthalmic formulations, eye ointments, powders, solutions, are also contemplated as being within the scope of this invention.

Rechargeable or biodegradable devices may also be used. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a drug at a particular target site.

Pharmaceutical compositions suitable for parenteral administration may include one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, and solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Depot injectable formulations are prepared by entrapping the drug in liposomes or microemulsions which are compatible with body tissue, or by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The optimum concentration of the active ingredient in the chosen medium can be determined empirically, according to procedures well known to medicinal chemists. As used herein, "biologically acceptable medium" includes any and all solvents, dispersion media, which may be appropriate for the desired route of administration of the pharmaceutical preparation. The use of such media for pharmaceutically active substances is known in the art. Except insofar as any conventional media or agent is incompatible with the activity of citalopram or escitalopram, its use in the pharmaceutical preparation of the invention is contemplated. Suitable vehicles and their formulation inclusive of other proteins are described, for example, in *Remington's Pharmaceutical Sciences*. These vehicles also include injectable "deposit formulations".

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the formulations. Examples of pharmaceutically acceptable antioxidants include: (1) water soluble antioxidants, such as ascorbic acid, cysteine hydrochloride, sodium bisulfate, sodium metabisulfite, sodium sulfite; (2) oil-soluble antioxidants, such as ascorbyl palmitate, butylated hydroxyanisole (BHA), butylated hydroxytoluene (BHT), lecithin, propyl gallate, alpha-tocopherol, and (3) metal chelating agents, such as citric acid, ethylenediamine tetraacetic acid (EDTA), sorbitol, tartaric acid, and phosphoric acid.

The invention now being generally described, it will be more readily understood by reference to the following examples, which are included merely for purposes of illustration of certain aspects and embodiments of the present invention, and are not intended to limit the invention.

EXAMPLES

Example 1

Synthesis of 4-[3-[1,3]-dioxolan-2-yl-1-(4-fluorophenyl)-1-hydroxypropyl]-3-hydroxymethylbenzonitrile To a suspension of 1-oxo-1,3-dihydro-isobenzofuran-5-carbonitrile 5 (15 g) in THF (50 mL, anhydrous) at 5-10° C. under argon was added 4-fluorophenylmagnesium bromide in ethyl ether (50 ml, 2 m). The reaction mixture was warmed to room temperature and stirred for 5 h. At that time, a second Grignard reagent prepared from 2-(2-bromoethyl)-1,3-dioxolane (25 g) with Mg powder in THF was added at room temperature. The reaction mixture was stirred at room temperature for 14 h. The reaction mixture was then quenched at 0° C. with aqueous ammonium chloride. The organic phase was separated and washed with water (50 mL), and concentrated to give a crude product. It was purified by flash chromatography (EtOAc:Hexane 1:1) to give 17 g of the titled product 5. $^1$H NMR (CDCl$_3$, 6): δ 1.54-1.66 (m, 1H), 1.75-1.88 (m, 1H), 2.18-2.30 (m, 1H), 2.36-2.47 (m, 1H), 356 (broad s, 1H), 3.80-4.00 (m, 4H), 4.10-4.17 (d, J=8 Hz, 1H), 4.22-4.30 (d, J=8 HZ, 1H), 4.86 (t, J=3 Hz, 1H), 5.50 (broad s, 1H), 6.8-7.10 (m, 2H), 7.16-7.26 (m, 2H), 7.50-7.70 (m, 3H). $^{13}$C NMR (CDCl$_3$, 6): δ 27.2, 35.8, 63.1, 64.9, 77.8, 103.4, 111.4, 114.7, 115.0, 118.3, 127.1, 127.6, 127.3, 131.1, 134.7, 141.1, 149.7, 159.9, 163.2.

Example 2

Synthesis of 1-(2-[1,3]-dioxolan-2-yl-ethyl)-1-(4-fluorophenyl)-1,3-dihydro-isobenzofuran-5-carbonitrile 4-[3-[1, 3]-Dioxolan-2-yl-1-(4-fluorophenyl)-1-hydroxypropyl-]3-hydroxymethylbenzonitrile (15 g) was dissolved in dichloromethane (150 mL) at room temperature, followed by addition of triethylamine (25 mL). The reaction mixture was cooled to 5-10° C. and stirred for 5 min, followed by addition of methane sulfonylchloride (8.4 g). The reaction mixture was warmed to room temperature and stirred for 10 min. It was quenched with 2% NaOH (100 mL) while maintained to 10-20° C. The organic phase was separated and was dissolved in water and concentrated to give 19.2 g crude product. $^1$H NMR (CDCl$_3$, δ): 1.42-1.57 (m, 1H), 1.63-1.76 (m, 1H), 2.20-2.38 (m, 2H), 3.78-3.96 (m, 4H), 4.84 (t, J=3 Hz, 1H), 5.18 (m, 2H), 7.00 (m, 2H), 7.38-7.50 (m, 4H), 7.60 (m, 1H). The product was separated into its enantiomers by CHIRALCEL OD=column using Methanol as eluent. Enantiomer 6a, 6.67 min; Enantiomer 6b, 8.30 min.

Example 3

Synthesis of 1-(4-Fluorophenyl)-1-(3-oxopropyl)-1, 3-dihydro-isobenzofuran-5-carbonitrile (7)

1-(2-[1, 3]-dioxolan-2-yl-ethyl)-1-(4-fluorophenyl)-1,3-dihydro-isobenzofuran-5-carbonitrile (6 g) was dissolved in a mixture of acetone (100 mL) and aqueous HCl (5N, 30 mL). The reaction mixture was stirred at room temperature for 60 h, and concentrated to remove acetone. The aqueous solution was extracted with ethyl acetate (40 mL), and concentrated to give a crude oil. It was dissolved in acetone (80 mL) and aqueous HCl (5N, 25 mL), stirred for 3 h, and concentrated to remove acetone. The aqueous solution was extracted with ethyl acetate (40 mL), washed with water, and concentrated to give the pure product 7 (5.6 g). $^1$H NMR (CDCl$_3$, δ): 2.22-2.64 (M, 4H), 5.14 (s, 2H), 6.94-7.06 (m, 2H), 7.40-7.63 (m, 5H), 9.70 (s, 1H).

Example 4

Synthesis of 2-Methyl-propane-2-sulfinic acid [3-[5-cyano-1-(4-fluorophenyl)-1,3-dihydro-isobenzofuran-1-yl]-propyl]-amide (8)

1-(4-fluorophenyl)-1-(3-oxopropyl)-1,3-dihydro-isobenzofuran-5-carbonitrile (3.0 g) was dissolved in THF (20 mL), followed by addition of (−)-tert-butylsulfinamide (1.5 g), and Ti (OEt)$_4$ (20 mL, Aldrich) in EtOH. The reaction mixture was stirred at room temperature for 10 min, and 55° C. for 1 h. The reaction mixture was cooled to 5-10° C., was added brine (50 mL), and EtOAc (150 mL). The reaction mixture was stirred at room temperature for 10 min and filtered. The EtOAc layer in the filtrate was separated and washed with brine and concentrated to give a crude oil. It was dissolved in THF (20 ml), cooled to 5-10° C. and added NaBH4 (1.6 g) Methanol (10 mL). The reaction mixture was stirred for 14 h, quenched with water at 5-10° C., extracted with EtOAc (100 mL). The extract was washed with brine and concentrated to give the crude product (3.5 g). It was passed through a silica gel column using EtOAc and hexane (8:2) to give the pure product (2.5 g) as a mixture of possible diastereomers. $^1$H NMR (CDCl$_3$, δ): 1.19 (s, 9H), 1.40-1.60 (m, 2H), 2.10-2.30 (m, 2H), 3.05-3.30 (m, 3H), 5.17 (m, 2H). 7.00 (m, 2H), 7.40-7.60 (m, 5H). $^{13}$C NMR(CDCl$_3$, δ): 22.4, 25.6, 38.1, 45.4, 55.4, 71.1, 90.7, 111.6, 115.1, 115.4, 118.4, 122.6, 125.1, 126.5, 126.6, 131.8, 139.1, 140.1, 149.0, 160.2, 163.5.

Example 5

Synthesis of 3-5-Cyano-1-(4-fluorophenyl)-1,3-dihydro-isobenzofuran-1-yl-propyl amine (didesmethylcitalopram)

2-Methyl-propane-2-sulfinic acid [3-[5-cyano-1-(4-fluorophenyl)-1,3-dihydro-isobenzofuran-1-yl]-propyl]-amide (2.0 g) was dissolved in methanol (35 mL) at room temperature, followed by addition of HCl (10%, 20 mL). The reaction mixture was stirred at room temperature for 16 h. The reaction mixture was concentrated to remove Methanol and added TBME (100 mL), water (50 mL), and aqueous potassium carbonate till basic. The organic phase was separated and washed with water (20 mL), brine (20 mL), and dried over sodium sulfate, concentrated to give an oil (1.3 g) as free base. $^1$H NMR (CDCl$_3$, δ): 1.23 (broad s, 2H), 1.21.30-1.43 (m, 2H), 2.08-2.25 (m, 2H), 2.63-70 (t, J=7 Hz, 2H), 5.10-5.20 (m, 2H). 7.00 (m, 2H), 7.38-7.60 (m, 5H).

Example 6

Synthesis of BOC-Didesmethylcitalopram (10)

To a solution of 3 (3.3 g) in dichloromethane (40 mL) was added triethylamine (10 mL) at room temperature, followed by addition of BOC anhydride (5.0 g). The reaction mixture was stirred for 1 h. The reaction mixture was then concentrated to a residue, which was passed through a flash silica gel column (EtOAc:Hexane 3:7) to give 3.5 product. $^1$H NMR (CDCl$_3$, δ): 1.30-1.50 (m, 2H), 1.41 (s, 9H), 2.06-2.28 (m, 2H), 3.15 (m, 2H), 4.54 (s, 1-1), 5.10-5.21 (m, 2H), 7.00-7.06 (m, 2H), 7.30-7.42 (m, 3H), 7.50 (s, 1H), 7.60 (d, J=8 Hz, 1H). The racemic product 10 was separated by CHIRALCEL OD column (Hexane:Ethanol 90:10) to give compound 10a (>99% ee, 7.20 min) and compound 10b (>99% ee, 8.4 min).

Example 7

Synthesis of (+)-Didesmethylcitalopram

Compound 10a (1.3 g) was dissolved in TFA (10 mL). It was stirred at room temperature for 1 h, and was concentrated to give a residue, which was added water (15 mL) and EtOAc (30 mL) and aqueous potassium carbonate till basic. Organic phase was separated and washed with water, brine, and concentrated to give the product (0.96 g, >95%).

(+)-DDCIT. [α]=+5.5° (C=1, Methanol). (−)-DDCIT was prepared similarly from compound 10b. Their $^1$H NMR spectra are the same as the racemate.

Example 8

Synthesis of Didesmethylcitalopram L-tartrate (11)

To a solution of the didesmethylcitalopram free base (1.3 g) in methanol (20 mL) was added a solution of L-tartaric acid (0.6 g) in water (5 mL). The reaction mixture was stirred for 30 min, and concentrated to give a white solid (1.8 g). $^1$H NMR (DMSO-d$_6$, δ): 1.26-1.60 (M, 2H), 2.24-2.30 (m, 2H), 2.70-2.80 (M, 2H), 4.03 (s, 2H), 5.10-5.25 (M, 2H), 7.15-7.20 (TM, 2H), 7.58-7.64 (M, 2H), 7.73-7.81 (M, 3H), 7.0-7.9 (broad, 4H). $^{13}$C NMR (DMSO-d$_6$, 5): 23.0, 17.8, 72.7, 91.1, 111.3, 115.8, 116.0, 119.5, 123.9, 126.4, 127.6, 127.7, 132.8, 140.6, 140.9, 149.7, 160.4, 163.7, 175.4. M+296.9.

Example 9

Synthesis of 1-(4-Fluorophenyl)-1-(3-methylaminopropyl)-1,3-dihydroisobenzofuran-5-carbonitrile) (Desmethylcitalopram)

1-(4-Fluorophenyl)-1-(3-oxopropyl)-1,3-dihydroisobenzofuran-5-carbonitrile (3.0 g) was dissolved in aqueous methylamine (10 mL, 40%). The reaction mixture was stirred for 2 h at room temperature. It was extracted with tert-butyl methyl ether (50 mL). The organic layer was washed with brine and concentrated to give a crude corresponding imine. It was dissolved in methanol (30 mL), and treated with sodium borohydride (2 g) at 10-20° C. for 30 min. The reaction mixture was then quenched with aqueous ammonium chloride (50 mL) and 5 N HCl until acidic. The reaction mixture was stirred for 10 min, followed by addition of potassium carbonate till basic (pH>9.5). This reaction mixture was then extracted with ethyl acetate (2×100 mL). The extracts were combined and washed with water, brine and concentrated to give the crude product. It was purified by flash chromatography (EtOAc:MeOH:Et$_3$N=8:1:1) to give 1.4 g titled product as free base. $^1$H NMR (CDCl$_3$, δ): 1.30-1.66 (m, 2H), 2.10-2.30 (m, 2H), 2.35 (s, 3H), 2.53-2.60 (m, 2H), 5.10-5.25 (m, 2H), 6.94-7.05 (m, 2H), 7.40-7:62 (m, 5H). $^1$H NMR (CDCl$_3$, δ): 23.9, 35.9, 38.8, 51.4, 71.2, 90.9, 111.5, 115.0, 115.3, 118.5, 122.7, 125.1, 126.6, 126.7, 131.7, 139.4, 140.2, 149.2, 160.2, 163.5. M+310.9.

(+)-Desmethylcitalopram was prepared similarly from enantiomerically pure 6a. [α]_+6. 0° (c=2, Methanol). (−)-Desmethylcitalopram was prepared from enantiomer 6b. [α]=−5.3° (c=2, Methanol).

Example 10

Synthesis of Desmethylcitalopram L-tartrate (12)

To a desmethylcitalopram (1.2 g) solution in Methanol (15 ML) was added a solution of L-tartaric acid (0.58 g) in water (2 mL). The reaction mixture was stirred at room temperature for 1 h.

The solvent was then removed to give the final salt. $^1$H NMR (DMSO-$d_6$, δ) 1.26-1.60 (m, 2H), 2.24-2.30 (m, 2H), 2.35 (s, 3H), 2.70-2 80 (m, 2H), 4.03 (s, 2H), 5.10-5.25 (m, 2H), 7.15-7.20 (tm, 2H), 7.58-7.64 (m, 2H), 7.73-7.81 (m, 3H), 7.0-7.9 (broad, 4H). $^{13}$C NMR (DMSO-$d_6$, δ): 21.4, 33.0, 37.8, 48.8, 71.9, 72.8, 91.1, 111.3, 115.8, 116.0, 119.5, 123.9, 126.4, 127.7, 132.8, 140.6, 140.8, 149.6, 159.8, 163.0, 175.5; M+310.9.

Example 11

Binding Data and In Vitro Results

Materials and Methods
  Binding Assays:
    The assays were performed using the following general procedures:

| Receptor | Origin | Reference Compound | Bibliography |
|---|---|---|---|
| NE transporter | Rat cerebral cortex | Protriptyline | Tejani-Butt, S. M., J. Pharmacol. Exp. Ther., 360; 427-436 (1992) |
| NE transporter (h) | Human recombinant (MDCK cells) | Protriptyline | Pacholczyk e al., Nature, 350; 350-354 (1991) |
| D1 (h) | Human recombinant (L cells) | SCJ 23390 | Zhou et al., Nature, 347; 76-80 (1990) |
| D2 (h) | Human recombinant (CHO cells) | (+) butaclamol | Grandy et al., Proc. Natl. Acad. Sci. USA, 86; 9762-9766 (1989) |
| D5, 4 (h) | Human recombinant (CHO cells) | Clozapine | Van Tol et al., Nature, 358; 149-152 (1992) |
| DA transporter | Rat striatum | GBR 12909 | Anderson, P. H., J. Neurochem 48: 1887-1896 (1987) |
| DA transporter (h) | Human recombinant (CHO cells) | GBR12909 | Anderson, P. H., J. Neurochem 48: 1887-1896 (1987) |
| M (non-selective) | Rat cerebral cortex | Atropine | Richards, Brit. J. Pharmacol., 99; 753-761 (1990) |
| 5-HT$_{1A}$ (h) | Human recombinant (CHO cells) | δ-OH-DPAT | Mulheron et al., J. Biol. Chem., 269; 12954-12962 (1994) |
| 5-HT$_{2A}$ | Rat cerebral cortex | Ketanserin | Leysen et al., Mol. Pharmacol. 21; 301-314 (1982) |
| 5-HT$_{2C}$ (h) | Human recombinant (CHO cells) | Mesulergine | Bonhaus et al., Brit. J. Pharmacol., 115; 622-628 (1995) |
| 5-HT transporter | Rat cerebral cortex | Zimelidine | Marcusson et al., J. Neurochem., 50; 1783-1790 (1988) |
| 5-HT transporter (h) | Human recombinant (HEK 293 cells) | Imipramine | Tatsumi et al., Eur. J. Pharmacol., 340; 249-258 (1997) |

The experimental conditions are summarized below:

| Receptor | Ligand | Conc. | Nonspecific | Incubation |
|---|---|---|---|---|
| NE Transporter | [$^3$H]nisoxetine | 1 nM | Desipramine (1 μM) | 240 min./4° C. |
| NE Transporter (h) | [$^3$H]nisoxetine | 0.3 nM | Desipramine (1 μM) | 60 min./4° C. |
| D1 (h) | [$^3$H]SCH 23390 | 0.3 nM | SCH 23390 (1 μM) | 60 min./22° C. |
| D2 (h) | [$^3$H]spiperone | 0.3 nM | (+)butaclamol (10 μM) | 60 min./22° C. |
| D4.4 (h) | [$^3$H]spiperone | 0.3 nM | (+)butaclamol (10 μM) | 60 min./22° C. |
| DA transporter | [$^3$H]GBR12935 | 0.8 nM | BTCP (100 μM) | 90 min./4° C. |
| DA transporter (h) | [$^3$H]GBR12935 | 0.5 nM | BTCP (10 μM) | 120 min./4° C. |
| M (non-selective) | [$^3$H]QNB | 0.05 nM | Atropine (1 μM) | 120 min./22° C. |
| 5-HT$_{1A}$ (h) | [$^3$H] δ-OH-DPAT | 0.3 nM | δ-OH-DPAT (10 μM) | 60 min./22° C. |
| 5-HT$_{2A}$ | [$^3$H]ketanserin | 0.5 nM | ketanserin (1 μM) | 15 min./37° C. |
| 5-HT$_{2C}$ (h) | [$^3$H]mesulergine | 0.7 nM | mesulergine (1 μM) | 30 min./37° C. |
| 5-HT transporter | [$^3$H]paroxetine | 0.05 nM | serotonin (100 μM) | 60 min./22° C. |
| 5-HT transporter (h) | [$^3$H]paroxetine | 0.1 nM | Imipramine (10 μM) | 30 min./22° C. |

Following incubation, the membranes were rapidly filtered under vacuum through glass fiber filters (GF/B, Packard or Filtermat A, Wallace). The filters were then washed several times with an ice-cold buffer using a cell harvester (Packard or Tomtec).

Bound radioactivity was measured with a scintillation counter (Topcount, Packard or Betaplate, Wallace) using a liquid scintillation cocktail (Microscint 0, Packard) or a solid scintillant (MeltiLex B/HS, Wallace).

Monoamine Uptake Assays

Compounds were evaluated in uptake assays for norepinephrine (NE), dopamine (DA) and serotonin (5-HT), using the following general procedure.

| Assay | Origin | Reference Compound | Bibliography |
|---|---|---|---|
| NE uptake | Rat hypothalamus | Protriptyline | Perovic, S. and Muller, W. E. G., Arzneimittelforschung Drug Res., 45,: 1145-1148 (1995) |
| DA uptake | Rat corpora striatum synaptosomes | GBR 12909 | Janowsky, A, et al., S. M. J. Neurochem. 46: 1272-1276 (1986) |
| 5 HT uptake | Rat brain synaptosomes | Imipramine | Perovic, S. and Muller, W. E. G., Arzneimittelforschung Drug Res., 45,: 1145-1148 (1995) |

Experimental conditions are summarized below:

| Assay | Tracer | Incubation | Reaction Process | Method of Detection |
|---|---|---|---|---|
| NE uptake | [$^3$H]NE (0.2 µCi/ml) | 20 min./ 37° C. | [$^3$H]NE incorporation into synaptosomes | Liquid scintillation |
| DA uptake | [$^3$H]DA (0.2 µCi/ml) | 15 min./ 37° C. | [$^3$H]DA incorporation into synaptosomes | Liquid scintillation |
| 5-HT uptake | [$^3$H]5-HT (0.2 µCi/ml) | 15 min./37° C. | [$^3$H]5-HT incorporation into synaptosomes | Liquid scintillation |

Radioactivity was determined with a scintillation counter (Topcount, Packard) using a liquid scintillation cocktail (Microscint 0, Packard).

Analysis and Expression of Results

For binding assays, the specific radioligand binding to the receptors is defined as the difference between total binding and nonspecific binding determined in the presence of an excess of unlabelled ligand. Results are expressed as a percent of control values and/or as a percent inhibition of control values obtained in the presence of the test compounds.

$IC_{50}$ values (concentration causing a half-maximal inhibition of control values) and Hill coefficients (nH) were determined by non-linear regression analysis of the inhibition curves. These parameters were obtained by Hill equation curve fitting. For binding assays, the inhibition constants ($K_i$) were calculated from the Cheng Prusoff equation ($K_i = IC_{50}/(1+L/K_D)$, where L=concentration of radioligand in the assay, and $K_D$=affinity of the radioligand for the receptor). The $IC_{50}$ values obtained for the reference compounds are within accepted limits of historic averages obtained ±0.5 log units.

Initial studies compared racemic forms of citalopram, desmethylcitalopram, and didesmethylcitalopram for their ability to inhibit the specific binding of radiolabeled ligands to several CNS receptors and neurotransmitter uptake sites for serotonin (5-HT), norepinephrine (NE) and dopamine (DA). Positive results from binding studies led to further evaluation in functional assays of monoamine uptake into rat brains synaptosomes. The compounds were tested first in the binding assays either at three or four concentrations and in the functional monoamine assays at seven or eight concentrations. In the human monoamine transporter binding assays, they were further tested at seven concentrations to obtain full competition curves. Each determination was made in duplicate. Results are shown in Table 1.

TABLE 1

Transport Binding and Functional Uptake Results

| | Transporter Binding $IC_{50}$ (nM) | | | Functional Uptake $IC_{50}$ (nM) | | |
|---|---|---|---|---|---|---|
| | 5-HT | DA | NE | 5-HT | DA | NE |
| Racemic citalopram | 6.6 | 3,920 | 36,900 | 2.5 | 17,000 | 3,600 |
| Racemic desmethyl-citalopram | 13 | 3,730 | 15,500 | 13 | 38,000 | 1,200 |
| Racemic didesmethyl-citalopram | 85 | 13,200 | 21,200 | 38 | 8,900 | 1,600 |
| Imipramine | 4.4 | | | 27 | | |
| Protriptyline | | 6.7/15 | | | 1.0 | |
| GBR12909 | | | 11 | | | 3.7 |

In addition to the results shown above, all three test articles, when tested at 1 µM, inhibited by <25% specific binding at the following receptors: dopamine-1 (D1), D2, D4.4, 5-HT1A, 5-HT2A, and 5-HT2C. At 1 µM, citalopram, desmethylcitalopram and didesmethylcitalopram inhibited [3H]-QNB binding to the nonselective muscarinic receptor by 33%, 20% and 12%, respectively.

Thus racemic citalopram and racemic forms of its mono- and didesmethyl metabolites selectively inhibit binding of 5-HT transporter, without affecting DA, NE uptake or ligand binding to several dopamine or 5-HT receptors.

Another in vitro study compared racemic citalopram, (R)(−)- and (S)(+)-desmethylcitalopram, and (R)(−)- and (S)(+)-didesmethylcitalopram were compared in the same binding assays as above. The compounds were tested in each assay at ten concentrations to obtain full competition curves. Each determination was made in duplicate. In each experiment, the respective reference compound was tested at a minimum of eight concentrations in duplicate to obtain an inhibition curve in order to validate this experiment. Results are shown in Table 2.

TABLE 2

Transporter and Muscarinic Receptor Binding

| | Transporter and Muscarinic Receptor Binding $IC_{50}$ (nM) | | | | |
|---|---|---|---|---|---|
| | 5-HT rat | 5-HT human | DA | NE | Muscarinic |
| Citalopram HBr (racemic) | 1.4 | 9.4 | 84,400 | 4,740 | 3,710 |

TABLE 2-continued

Transporter and Muscarinic Receptor Binding

Transporter and Muscarinic Receptor Binding $IC_{50}$ (nM)

| | 5-HT rat | 5-HT human | DA | NE | Muscarinic |
|---|---|---|---|---|---|
| (R)(−)-Desmethyl-citalopram | 11 | 42 | 58,000 | 920 | 15,400 |
| (S)(+)-Desmethyl-citalopram | 1.3 | 20 | 79,500 | 11,500 | 5,290 |
| (R)(−)-Didesmethyl-citalopram | 27 | 14 | 14,100 | 3,620 | 34,900 |
| (S)(+)-Didesmethyl-citalopram | 19 | 219 | 71,100 | 20,100 | 15,800 |
| Zimelidine | 57 | | | | |
| Imipramine | | 11 | | | |
| GBR12909 | | | 6.3/25 | | |
| Protriptyline | | | | 6.3 | |
| Atropine | | | | | 0.33 |

(R)(−)- and (S)(+)-desmethylcitalopram inhibited the specific binding of [³H]-paroxetine to both rat brain-derived and human 5-HT transporters, with the (S) isomer appearing to have an approximately 10-fold higher affinity than its antipode in rat brain and two-fold greater affinity for the human form. (R)(−)- and (S)(+)-didesmethylcitalopram had lower affinities for the 5-HT transporter, compared to citalopram and mono-desmethylcitalopram, but still retained potent and selective affinity for this transporter. The two enantiomers of desmethylcitalopram had comparable affinities for the rat brain 5-HT transporter, whereas (S)-didesmethylcitalopram enantiomer showed a 16-fold higher affinity for the human 5-HT transporter. All forms of desmethyl and didesmethylcitalopram had low affinities for the NE and DA transporter, as well as the nonspecific muscarinic receptor. Thus, both desmethyl and didesmethylcitalopram retain potent 5-HT transporter inhibitory activity and selectivity for this transporter comparable to or greater than the parent compound, citalopram.

The above study compared racemic citalopram and enantiomers of its desmethyl and didesmethyl forms in receptor binding assays. Functional uptake assays were also performed, where racemic citalopram, (R)- and (S)-desmethylcitalopram, and (R)- and (S)-didesmethylcitalopram were compared for their ability to inhibit the uptake of the radiolabeled 5-HT, NE and DA into rat brain synaptosomes. The same compounds also were tested for their ability to inhibit the specific binding of [³H]-nisoxetine and [³H]-GBR 12935 to the NE and DA transporters in human recombinant MDCK and CHO cells, respectively. The latter two assays represent follow up from the study described above, which examined the specific binding of the same test articles to the human 5-HT transporter. In each assay the compounds were tested at ten concentrations to obtain full competition curves. Each determination was made in duplicate. In each experiment, the respective reference compound was tested at a minimum of eight concentrations in duplicate to obtain an inhibition curve in order to validate this experiment. Results are shown in Table 3.

TABLE 3

Monoamine Uptake and Human Transporter Binding Results

| | Monoamine Uptake IC50 (nM) | | | Human Transporter Binding IC50 (nM) | |
|---|---|---|---|---|---|
| | 5-HT | DA | NE | NE | DA |
| Citalopram HBr (racemic) | 2.2 | 13,000 | 4,900 | 4,600 | 38,800 |
| (R)(−) Desmethyl-citalopram | 110 | 9,400 | 1,700 | 815 | 37,600 |
| (S)(+) Desmethyl-citalopram | 5.8 | 7,600 | 4,100 | 10,300 | 27,700 |
| (R)(−) Didesmethyl-citalopram | 130 | 27,000 | 1,300 | 5,520 | 38,900 |
| (S)(+) Didesmethyl-citalopram | 180 | 11,000 | 3,300 | 24,200 | 54,700 |
| Imipramine | 25 | | | | |
| GBR12909 | | 3.1 | | | 8.1 |
| Protriptyline | | | 2.3 | 5.2 | |

Racemic citalopram and (S)-desmethylcitalopram were both potent inhibitors of [3H]-5-HT uptake, with IC50 values of 2.2 and 5.8 nM, respectively. (R)-Desmethylcitalopram was approximately ½0th as potent as (S)-desmethylcitalopram in inhibiting [3H]-5-HT uptake. Removal of the second methyl group resulted in an approximately 70-fold decline in potency, but the two stereoisomers of didesmethylcitalopram did not differ greatly in inhibiting 5-HT uptake. Citalopram and all metabolites thereof were much less potent inhibitors of [3H]-NE and [3H]-DA uptake than the controls. These results correlated well with negligible effects on the specific binding of [3H]-nisoxetine and [3H]-GBR-12935 to the human NE and DA transporters, respectively.

In conclusion, citalopram and its metabolites were selective for inhibiting functional 5-HT uptake or specific binding to the 5-HT transporter vis-a-vis DA and NE. In the aggregate, these functional uptake and receptor binding studies clearly show that, contrary to what the literature teaches, the metabolites of citalopram retain potent and selective inhibitory properties on the 5-HT reuptake transporter.

Example 12

Evaluation of In Vivo Efficacy

The value of a therapeutic agent in the treatment of migraine may be evaluated using an animal model. Various models are known in the art as being predictive of migraine therapies, including the following model. It should be noted that the predictive value of any model may be limited to therapeutic agents that operate via the mechanism that the model is based on, and may not be useful for evaluating those that operate differently. In such cases, an alternative model should be sought.

Neurogenic Plasma Estravasation in the Dural Layer Induced by Electrical Stimulation Harlan Sprague-Dawley rats (225-325 g) or guinea pigs from Charles River Laboratories (225-325 g) are anesthetized with sodium phenobarbitol (65 mg/kg or 45 mg/kg, respectively, intraperitoneally) and placed in a stereotaxic frame (David Kopf Instruments) with the incisor bar set at −3.5 mm for rats or −4.0 mm for guinea pigs. Following a midline sagittal scalp incision, two pairs of bilateral holes are drilled through the skull (6 mm posteriorly, 2.0 and 4.0 mm laterally for rats; 4 mm posteriorly and 3.2 and 5.2 mm laterally for guinea pigs—all coordinates reference to bregma). Pairs of stainless steel stimulating electrodes, insulated except for the tips, are lowered through the holes in both hemispheres to a depth of 9 mm (rats) or 10.5 mm (guinea pigs) from dura.

The femoral vein is exposed and a dose of the test compound is injected intravenously (1 ml/kg). Approximately seven minutes later, a 50 mg/kg dose of Evans Blue, a fluorescent dye, is also injected intravenously. The Evans Blue complexes with proteins in the blood and functioned as a marker for protein extravasation. Exactly ten minutes post-injection of the test compound, the left trigeminal ganglion is stimulated for three minutes at a current intensity of 1.0 mA (5 Hz, 4 msec duration) with a potentiostat/galvanostat.

Fifteen minutes following the stimulation, the animals are killed and exanguinated with 20 ml of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope equipped with a grating monochromator and a spectrophotometer is used to quantify the amount of Evans Blue dye in each tissue sample An excitation wavelength of approximately 535 nm is utilized and the emission intensity at 600 nm is determined. The microscope is equipped with a motorized stage and is interfaced with a personal computer. This facilitated the computer-controlled movement of the stage with fluorescence measurements at 25 points (500 μm steps) on each dural sample. The mean and standard deviation of the measurements are determined by the computer.

The dural extravasation induced by electrical stimulation of the trigeminal ganglion is an ipsilateral effect (i.e. it occurs only on the side of the dura in which the trigeminal ganglion was stimulated). This allows the other, unstimulated, half of the dura to be used as a control. The ratio of the amount of extravasation in the dura from the stimulated side compared to the unstimulated side is calculated. Saline controls yielded a ratio of approximately 2.0 in rats and 1.8 in guinea pigs. In contrast, a compound which effectively prevents the extravasation in the dura from the stimulated side would have a ratio of approximately 1.0. A dose-response curve is generated and the dose that inhibited the extravasation by 50% ($ID_{50}$) is estimated.

The invention claimed is:

1. A method for treating migraine, said method comprising administering to a subject in need thereof a composition consisting of a therapeutically effective amount of escitalopram, or pharmaceutically acceptable salt thereof and a pharmaceutically acceptable carrier.

2. The method according to claim 1, wherein the migraine is migraine without aura or migraine with aura.

3. A method for treating or alleviating pain associated with migraine, said method comprising administering to a subject in need thereof a composition consisting of a therapeutically effective amount of escitalopram, or pharmaceutically acceptable salt thereof and a pharmaceutically acceptable carrier.

4. A method according to claims 1, 2, or 3, wherein said therapeutically effective amount ranges from about 0.5 mg/day to about 500 mg/day.

5. A method according to claims 1, 2, or 3, wherein said therapeutically effective amount ranges from about 1 mg/day to about 250 mg/day.

6. A method according to claims 1, 2, or 3, wherein said therapeutically effective amount ranges from about 5 mg/day to about 100 mg/day.

7. A method according to claims 1, 2, or 3, wherein said therapeutically effective amount is administered orally.

8. A method according to claim 7 wherein said therapeutically effective amount is administered in the form of a capsule or tablet.

9. A method according to claims 1, 2, or 3, wherein said therapeutically effective amount is administered parenterally.

10. A method according to any of claims 1, 2, or 3, wherein the subject is a human.

* * * * *